United States Patent

Mougin et al.

[11] Patent Number: 6,166,093
[45] Date of Patent: *Dec. 26, 2000

[54] COSMETIC OR DERMATOLOGICAL COMPOSITIONS OF POLYURETHANE AND/OR POLYUREA BLOCK POLYCONDENSATION PRODUCTS CONTAINING SILICONE GRAFTS AND THEIR USE

[75] Inventors: Nathalie Mougin, Paris; Jean Mondet, Aulnay sous Bois, both of France

[73] Assignee: L'Oréal, Paris, France

[*] Notice: This patent issued on a continued prosecution application filed under 37 CFR 1.53(d), and is subject to the twenty year patent term provisions of 35 U.S.C. 154(a)(2).

[21] Appl. No.: 08/672,092

[22] Filed: Jun. 27, 1996

[30] Foreign Application Priority Data

Jun. 27, 1995 [FR] France .................................... 95 07731

[51] Int. Cl.$^7$ .................................................. A61K 47/34
[52] U.S. Cl. ................................... 514/772.1; 514/772.3; 424/70.12; 424/401; 523/105; 525/452; 525/453; 525/474
[58] Field of Search ............................. 523/105; 424/401, 424/70.12; 525/452, 453, 474; 514/772.1, 772.3

[56] References Cited

U.S. PATENT DOCUMENTS 5,059,707 10/1991 Motegi ..................................... 556/449
5,643,581 7/1997 Mougin .................................. 424/401

FOREIGN PATENT DOCUMENTS

| 0 277 816 | 2/1988 | European Pat. Off. . |
| 0 324 946 | 12/1988 | European Pat. Off. . |
| 0 636 361 | 7/1994 | European Pat. Off. . |
| 2 645 156 | 3/1990 | France . |

*Primary Examiner*—Patricia A. Short
*Attorney, Agent, or Firm*—Finnegan, Henderson, Farabow, Garrett & Dunner, L.L.P.

[57] ABSTRACT

Cosmetic or dermatological compositions, especially in the field of hair care, make-up and beauty or hygiene products, of polyurethane and/or polyurea block polycondensation products comprising a chain formed by the repetition of at least one polyurethane and/or polyurea block -[-M-]- containing a polysiloxane graft.

The polycondensation compositions are preferably multi-block and comprise a chain which is also formed by the repetition of a polyurethane and/or polyurea block -[-N-]- containing nonionic groups and/or ionic groups and/or a polyurethane and/or polyurea block -[-G-]- containing oligomers of organic polymers and/or a polysiloxane block -[-L-]-.

12 Claims, No Drawings

COSMETIC OR DERMATOLOGICAL COMPOSITIONS OF POLYURETHANE AND/OR POLYUREA BLOCK POLYCONDENSATION PRODUCTS CONTAINING SILICONE GRAFTS AND THEIR USE

The present invention relates to the use in and for the production of cosmetic or dermatological compositions, especially in the field of hair care, make-up, and beauty or hygiene products, of polyurethane and/or polyurea block polycondensation products comprising a chain formed by the repetition of at least one polyurethane and/or polyurea block -[-M-]- containing a polysiloxane graft.

In cosmetic formulations it is common to employ film-forming organic polymers in order to provide properties of form retention and fixation of the hair in styling products applied with rinsing and without, eyelash-sheathing properties in mascaras, protective coating properties in nail varnishes or skin care products, and adhesion properties in make-up products such as compact powders, foundations, eyeliners or skin care products.

These various properties are in general linked to the film-forming characteristics of the organic polymer, especially the mechanical properties and the surface energy (adhesion).

It is also common to use silicones in the form of oils, gums or waxes in order to additionally provide the treated keratinous materials with surface properties such as sheen or gloss in the field of hair care products, mascaras or nail varnishes, lubricity, permanence with respect to water, and softness to the touch without a greasy appearance. The use of more or less fluid silicones makes it possible to obtain these properties, but such silicones, once applied to the hair, nails, eyelashes or skin, are not durable owing to the fact that they have inadequate mechanical properties.

In recent years, particular interest has become evident in the realization of film-forming cosmetic compositions comprising a combination of one or more film-forming organic polymers with one or more silicones.

However, these combinations do not provide the additive effect of the properties specific to each constituent of these combinations. The silicones with the greatest performance, namely the polydimethylsiloxanes and polymethylphenylsiloxanes, are in fact incompatible with the majority of the organic polymers in the formulation.

On the other hand, in order for these combinations to be able to provide the expected properties, it is necessary for the mixtures of these constituents to lead to stratification following application and drying. The film-forming polymer must go into direct contact with the hair, eyelash, nail or skin, and must provide good adhesion, whereas the silicone must, preferably, go to the surface, in order to provide the surface with characteristics of sheen or gloss, lubricity, softness to the touch and permanence with respect to water. It is therefore difficult simply by mixing film-forming polymers and silicones in one formulation to obtain, simultaneously, good compatibility of the constituents and an additive effect of their properties.

To overcome these disadvantages, multiblock polycondensation products are known whose chain is formed from at least one polyurethane and/or polyurea block and which comprise anionic or cationic groups and at least one polysiloxane block. They are described in the patent application EP-A-0 636 361, the disclosure of which is specifically incorporated by reference herein.

In order to obtain good surface properties specific to the silicones, these multiblock copolymers must comprise a large quantity of polysiloxane blocks in the chain, which has the disadvantage of reducing the film-forming properties, and especially the mechanical properties, which are desired for the various cosmetic applications (excessively soft or elastomeric films). This type of copolymer is used only in aqueous dispersion in the form of a pseudo-latex; this considerably limits the possibilities for their use in other forms of formulations, such as organic or aqueous-organic solutions, and, in particular, for the preparation of anhydrous formulations, such as lipsticks, waterproof mascaras and make-up powders.

The inventors have surprisingly discovered new block polycondensation products, as well as new uses for block polycondensation products of the prior art. The claimed invention pertains to use of block polycondensation products whose chain is formed by the repetition of at least one polyurethane and/or polyurea block comprising a polysiloxane graft.

The polymers according to the present invention can provide good adhesion characteristics to the hair, eyelashes, nails and skin. They can make it possible to obtain deposits or coatings which are highly permanent to the action of water, or water in the presence of surfactants. At the surface, moreover, these deposits can exhibit the characteristics of silicones, namely sheen or gloss, lubricity, permanence and softness to the touch. These deposits can retain advantageous mechanical properties when the polymers of the invention are used alone or in combination with other organic polymers.

The polyurethane and/or polyurea polycondensation products containing silicone grafts of the invention can make it possible to obtain a good additive effect of the film-forming properties of the polyurethanes and/or polyureas and surface characteristics of the silicones.

In comparison to the polyurethane and/or polyurea polycondensation products with silicone blocks of the prior art, they also can have surface properties, imparted by the silicones, which are substantially improved, such as sheen or gloss, lubricity, softness to the touch and permanence with respect to water, without impairment of the film-forming properties of the polymer.

The block polycondensation products according to the invention can have the advantage of being compatible with conventional silicones and/or other additional organic polymers which are also present in the same formulation. Owing to their silicone-grafted chain, they can make it possible to combine these conventional silicones with these additional organic polymers.

The block polycondensation products according to the invention may be anionic, cationic, amphoteric, nonionic, or zwifterionic in nature and are insoluble in water. Their structure permits their use not only in aqueous dispersions in the form of a pseudo-latex, the definition of which will be given below, but also in solution in an organic solvent, thereby opening up greater possibilities for cosmetic formulations.

The polyurethane and/or polyurea block polycondensation products used according to the invention are characterized in that their chain is formed by the repetition of at least one polyurethane and/or polyurea block -[-M-]- comprising a polysiloxane graft.

The number-average molecular weights of the silicone-grafted polyurethane and/or polyurea polycondensation products can vary within wide limits, preferably ranging from 2000 to 500,000, and more preferably from 3000 to 250,000.

The polycondensation products according to the invention are preferably multiblock, and their chain, in addition to containing the repetition of at least one block -[-M]- described above also contains the repetition of a polyurethane and/or polyurea block -[-N-]- containing nonionic and/or anionic, cationic, amphoteric or zwitterionic groups and/or the repetition of a polyurethane and/or polyurea block -[-G-]- containing oligomers of organic polymers and/or the repetition of a polysiloxane block -[-L-]-.

The various blocks -[-M-]-, -[-N-]-, -[-G-]- and -[-L-]- forming the chain of the multiblock polycondensation products of the invention are preferably distributed randomly.

For ready comprehension of the following description, and in particular of the definition of the formulae given, an explanation will first be given, but only in very general terms, of the general process for the synthesis of the block polycondensation products of the invention. The details of the process will be given further below. Similarly, the definitions and values of certain radicals and other parameters will be given further below.

The polycondensation products according to the invention can be prepared by a process which comprises at least one conventional reaction step of polycondensation between (I) a polysiloxane oligomer having a diol or diamine function at only one end, of formula:

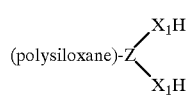
(1)

and (ii) a diisocyanate of formula:

$$O=C=N-R-N=C=O \quad (2).$$

A polycondensation product is obtained which is formed by the repetition of a polyurethane and/or polyurea sequence grafted by a polysiloxane, corresponding to the formula:

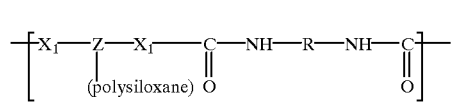
(3)

In the formulae (1), (2) and (3), $X_1$ represents, separately or jointly, —O— or —NH—, and Z represents a trivalent hydrocarbon radical which may contain one or more heteroatoms such as oxygen, sulphur and nitrogen.

If it is desired to obtain multiblock polycondensation products whose chain also comprises the repetition of a polysiloxane block -[-L-]-, in this same step a polysiloxane polymer having a hydroxyl or amine function at its chain ends (i.e. an α,ω-dihydroxy-polysiloxane, an α,ω-diaminopolysiloxane or an alcohol amine polysiloxane) is reacted with the diisocyanate in a quantity sufficient to react with the two types of reactive polysiloxane oligomers.

A multiblock polycondensation product is thus obtained which additionally comprises, in the chain, the repetition of a polysiloxane block of formula:

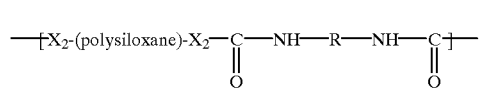
(4)

If it is desired to obtain multiblock polycondensation products whose chain is extended with the repetition of a polyurethane and/or polyurea block -[-N-]- containing nonionic groups and/or ionic groups and/or a polyurethane and/or polyurea block -[-G-]- comprising oligomers of an organic polymer, the chains of the polycondensation product obtained previously are coupled by means of a coupling agent (in a variable quantity chosen depending on the final chain length desired) chosen from diols and/or diamines and/or alkanol amines in order to obtain, finally, a new polycondensation product with a longer chain, comprising ionic groups and/or nonionic groups and/or oligomers of an organic polymer.

In the second step, the alcohol and/or amine functions of the coupling agent (which agent can conveniently be symbolized here by OH—B—OH, NH$_2$—B—NH$_2$, NH$_2$—B—OH, OH—E—OH, NH$_2$—E—NH$_2$, NH$_2$—E—OH) then react, in accordance with the same mechanisms as those set out for the first step, either with the isocyanate functions carried at the chain end by the silicone-grafted polycondensation product obtained above or with the isocyanate functions carried by the free diisocyanate when the latter was introduced in a stoichiometric excess during the first step, thereby giving rise, in the (longer) chain of the new polycondensation product obtained, to a succession of urethane and/or urea units, i.e. to blocks of the polyurethane and/or polyurea type which can be symbolized by the formulae:

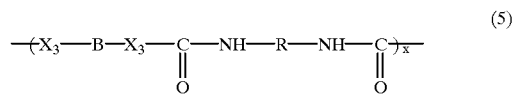
(5)

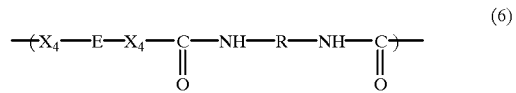
(6)

in which $X_3$ and $X_4$ represent —O— or —NH— and x is a value which corresponds substantially to the number of moles of coupling agent employed in the reaction.

As indicated above, a multiblock polycondensation product is finally obtained in this way which is formed by the repetition of silicone-grafted blocks of the formula (3), optionally of polysiloxane blocks (4) and/or of polyurethane and/or polyurea blocks of formula (5) and/or of formula (6).

The coupling agents corresponding to the formula (V) (i.e. the radical B) can comprise chemically anionizable or cationizable groups, i.e. groups which, respectively, when subjected to the action of a base, give anionic groups (in the case for example of carboxylic groups) and, when subjected to the action of an acid, give cationic groups (as in the case for example of a tertiary amine). The neutralization of the anionizable (or, respectively, cationizable) groups by the base (or, respectively, by the acid) can then be chosen to be either partial or total depending on the quantities of neutralizing agents employed.

The ionizable (and, after neutralization, ionized) character of the polycondensation product thus makes it possible to do without the use of surfactants during the preparation of the corresponding pseudo-latices (autodispersibility). These pseudo-latices are obtained by the conventional methods which are known for the preparation of pseudo-latices, with the proviso, however, of certain particular features which will be mentioned in more detail later on. In particular, it may be stressed again that the pseudo-latices according to the invention have a more or less marked ionic character.

The other coupling agents, corresponding to the formula (6) (i.e. the radical E), are oligomers of an organic polymer comprising a diol, diamine or alcohol-amine function at the chain end.

The polyurethane and/or polyurea block -[-M-]- containing a polysiloxane graft is preferably of the following general formula (I):

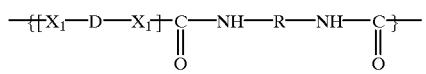 (I)

in which:
X₁ represents, separately or jointly, —O—or —NH—;
D is a segment of formula:

Z is a trivalent hydrocarbon radical which may contain one or more heteroatoms such as oxygen, sulphur and nitrogen;
Q is a polysiloxane segment;
R (which is just the unit of the diisocyanate as mentioned above) is a divalent radical chosen from the alkylene radicals of aliphatic, cycloaliphatic or aromatic type.

The polysiloxane segment Q is preferably of the following general formula (I'):

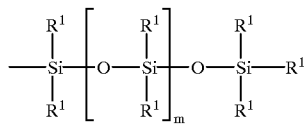 (I')

in which the radicals $R^1$ are identical or different and are chosen from $C_1$–$C_{20}$ monovalent hydrocarbon, halohydrocarbon or perhalogenated radicals which are free or substantially free from ethylenic unsaturation, and also from aromatic radicals, and m is an integer such that the average molecular weight, measured at the top of the GPC peak of the polysiloxane segment, preferably ranges from 300 to 50,000, and more preferably from 500 to 20,000.

Z is preferably a trivalent radical chosen from the alkyl or ether radicals of the type:

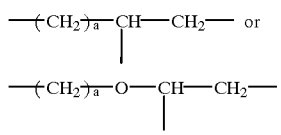

in which a represents an integer ranging from 1 to 10.

Suitable radicals $R^1$ within the scope of the invention are more particularly alkyl radicals, and especially methyl, ethyl, propyl, isopropyl, butyl, pentyl, hexyl, octyl, decyl, dodecyl and octadecyl radicals, cycloalkyl radicals, especially the cyclohexyl radical, aryl radicals, especially phenyl and naphthyl, arylalkyl radicals, especially benzyl and phenylethyl, and tolyl and xylyl radicals.

It should be noted that, according to the invention, it is important for the polysiloxane segment to be free or substantially free from units of the type Si—H or Si—$R^1$ in which $R^1$ represents a radical having ethylenic unsaturation, in order to avoid any premature crosslinking of the polycondensation product with itself.

Dealing now with the polysiloxane blocks -[-L-]- which occur in the composition of the polycondensation products which are utilized within the scope of the invention, these blocks are preferably of the following general formula (II):

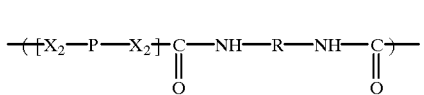 (II)

in which:
P is a polysiloxane segment;
$X_2$ represents, separately or jointly, —O—or —NH—;
and R (which is just the unit of the diisocyanate as mentioned above) is a divalent radical chosen from the alkylene radicals of aromatic, aliphatic or cycloaliphatic type.

The polysiloxane segment P is preferably of the following general formula (II'):

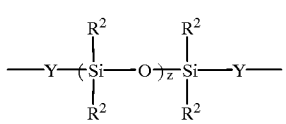 (II')

in which the radicals $R^2$, which may be identical or different, are as defined for $R^1$ above, Y represents a divalent hydrocarbon radical which may contain one or more heteroatoms such as oxygen, sulphur or nitrogen, and z is an integer which is such that the average molecular weight, measured at the top of the GPC peak of the polysiloxane segment, preferably ranges from 300 to 50,000, and more preferably from 500 to 20,000.

Y is preferably a divalent radical chosen from the alkylene radicals of the formula —$(CH_2)_b$—in which b represents an integer which can range from 1 to 10.

According to a particularly preferred embodiment of the invention, the polysiloxane segment P which is present in the polycondensation products is of the following formula (II'):

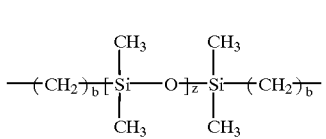 (II″)

in which b and z are values as defined above.

With regard to the polyurethane and/or polyurea blocks -[-N-]- which can be present in the composition of the polycondensation products of the invention, these blocks are preferably of the following general formula (III):

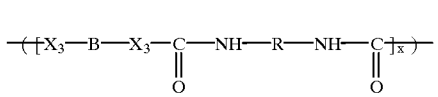 (III)

in which:
$X_3$ represents, separately or jointly, —O—or —NH—;
R (which, as above for the formula (I), is just the unit of the diisocyanate used to carry out the condensation reaction) is as defined above for the blocks of formula (I);
x (which, as indicated above in the description, corresponds substantially to the number of moles of coupling agent used in the process for the synthesis of the polycondensation product) is an integer which can preferably vary from 1 to 10, and more preferably from 1 to 4, and B (which is just the unit provided by the coupling agent as mentioned above) is a divalent hydrocarbon radical which carries a positive or negative ionic charge or else a nonionic divalent hydrocarbon radical.

Radicals B which carry anionic groups (i.e. negative charges) are more particularly those which carry a group having one or more carboxylic functions and/or one or more sulphonic functions, the carboxylic and/or sulphonic functions being partially or totally neutralized by an inorganic or organic base, as will be explained in more detail later on.

Thus, among the divalent radicals B which carry carboxylic or sulphonic functions and which are preferred for use in the scope of the present invention, mention may be made of those of formula (IV):

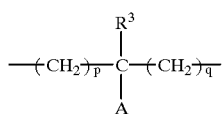
(IV)

in which $R^3$ represents a linear or branched $C_1$–$C_3$ alkyl radical, A represents a carboxylic acid function (—COOH) or sulphonic acid function (—SO$_3$H) or a salt of said acid functions (carboxylate and sulphonate functions, respectively), and p and q, which may be identical or different, represent integers ranging from 1 to 5, and more preferably those of formula (IV'):

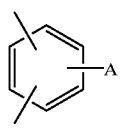
(IV')

in which A has the above meaning.

Radicals B which carry cationic groups (i.e. positive charges) are more particularly those which carry groups of the tertiary amine type, the said tertiary amines being, partially or totally, either neutralized (presence of —NH$^+$— units) or quaternized, or betainized, as will be explained in more detail later on.

Thus, among the divalent radicals B which carry cationizable tertiary amine functions and which are preferred in the scope of the present invention, mention may be made of those of formula:

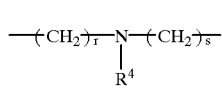
(V)

in which $R^4$ represents a linear or branched $C_1$–$C_4$ alkyl radical and r and s are two identical or different integers which may range from 1 to 10.

In neutralized, quaternized or betainized form, the above radicals B then become:

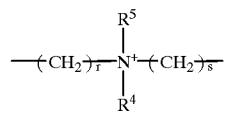
(V')

in which formula $R^4$ is as defined above and $R^5$ represents either hydrogen (neutralization) or a linear or branched $C_1$–$C_{10}$ alkyl radical or an aromatic ring (quaternization); or else a linear or branched $C_1$–$C_{10}$ alkyl radical which carries a carboxylate or sulphonate group (betainization).

Nonionic radicals B which can be mentioned are units provided by aliphatic, cycloaliphatic or aromatic α,ω-diols, such as ethylene glycol, propylene glycol, 1,4-butanediol and cyclohexanedimethanol; aliphatic, cycloaliphatic or aromatic α,ω-diamines, such as diaminopropane; or by aliphatic, cycloaliphatic or aromatic alcohol-amines, such as alkanolamines (ethanolamine).

In the above definitions of B, when the block -[-N-]- of formula (III) repeats itself (x greater than 1), two or more different types of B may be present in the final structure of the polycondensation product with, in particular, a combination between nonionic radicals B and other radicals B which carry anionic or cationic groups. It is preferable to avoid the coexistence in the same chain of anionic groups B and cationic groups B.

The blocks -[-N-]- which are present in the structure of the chain of the multiblock polycondensation products of the invention are polyurethane and/or polyurea blocks which provide the rigidity, polarity and optionally the polyelectrolyte character for the possibility of dispersion in water.

With regard to the polyurethane and/or polyurea blocks comprising oligomers of organic polymer, -[-G-]-, which may occur in the composition of the multiblock condensation products according to the invention, these former blocks are preferably of the following general formula (VI):

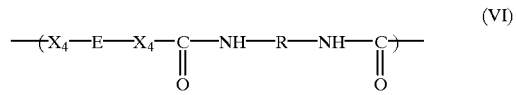
(VI)

in which:

$X_4$ represents, separately or jointly, —O— or —NH—,

R (which as above for the formula (1) is just the unit of the diisocyanate used to carry out the condensation reaction) is as defined above, and E (which is just the unit provided by the oligomer coupling agent as mentioned above) is an oligomer of a polyether, of an aliphatic and/or cycloaliphatic and/or aromatic polyester obtained by condensation of one or more aliphatic, cycloaliphatic and/or aromatic diacids and of one or more aliphatic, cycloaliphatic and/or aromatic diols; or a polyester amide or a polyamide, preferably hydrophilic.

Examples which may be mentioned of the polyethers are polyoxyethylenes, polyoxypropylenes, ethylene oxide-propylene oxide copolymers, and polyoxytetramethylenes. Among the polyesters mention may be made of poly-ε-caprolactam.

Since the blocks -[-G-]- of formula (VI) are repeating, different values of E may occur in the structure of the final polymer. In other words, the repeating blocks -[-G-]- in the final polymer can be different in structure. The same is true for blocks -[-M-]-, -[-N-]- and -[-L-]-. For example, in block -[-N-]-, different values of B may occur in the structure of the final polymer, and in block -[-L-]-, different values of P may occur in the structure of the final polymer.

The chain lengths of each oligomer E are preferably such that their average molecular weight, measured at the top of the GPC peak, preferably ranges from 300 to 70,000.

The oligomer segments E may contain ionizable grafts on the chain or ionizable groups in the chain, promoting the dispersion in water of the final polymer.

The blocks -[-G-]- present in the structure of the chain of the multiblock polycondensation products of the invention are also polyurethane and/or polyurea blocks which provide the rigidity, the polarity and possibly the polyelectrolyte character for the possibility of dispersion in water.

Finally, as regards the radicals R which are particularly preferred according to the present invention and which occur within the scope of the definition of the blocks of formulae (I) to (VI) given above, it is possible to mention those of formulae:

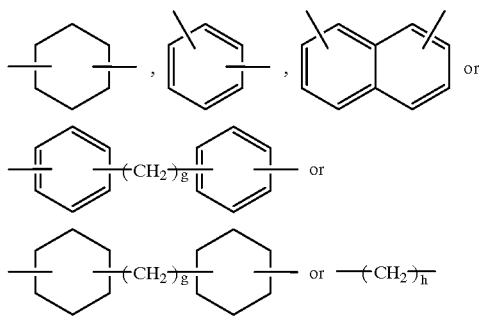

in which g is an integer ranging from 0 to 3, and h is an integer preferably ranging from 1 to 20, and more preferably from 2 to 12.

Among the particularly preferred divalent radicals R occurring within the scope of the above formulae, mention may be made of the radicals hexamethylene, 4,4'-biphenylenemethane, 2,4- and/or 2,6-tolylene, 1,5-naphthylene, p-phenylene, 4,4-biscyclohexylmethylene and the divalent radical derived from isophorone.

The preferred block polycondensation products according to the invention are characterized in that their chain is formed with a repetition of at least one sequence -[-M-]- which carries a silicone graft and at least one polyurethane and/or polyurea block -[-N-]-and/or a polyurethane and/or polyurea block -[-G-]- providing the properties of rigidity and being able to permit dispersion in water (pseudo-latex).

Among the polycondensation products according to the invention of the polyurethane and/or polyurea type with polysiloxane grafts, as defined above, some are novel and constitute a subject of the invention. These are polyurethane and/or polyurea polycondensation products with polysiloxane grafts, characterized in that the chain is formed by the repetition of at least one polyurethane and/or polyurea block -[-M-]- containing a polysiloxane graft, and also:
(i) by the repetition of a polyurethane and/or polyurea block -[-N-]- of the following general formula (III):

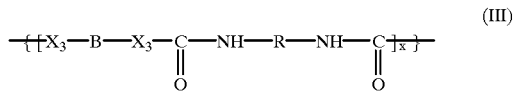

(III)

in which:
X$_3$ represents, separately or jointly, —O—or —NH—;
R is a divalent radical chosen from alkylene radicals of the aliphatic, cycloaliphatic or aromatic type;

x is an integer ranging from 1 to 10;
the radicals B, which are identical or different, are divalent hydrocarbon radicals which carry nonionic groups chosen from the units provided by the α,ω-diols; the α,ω-diamines and the aliphatic, cycloaliphatic or aromatic alcohol-amines; or which carry anionic groups having one or more carboxylic functions and/or one of the sulphonic functions, the said carboxylic and/or sulphonic functions being partially or totally neutralized by an inorganic or organic base, or else which carry tertiary amine groups, the said tertiary amines being, partially or totally, either neutralized by an inorganic or organic base, or quaternized, or else betainized; and/or
(ii) by the repetition of a polyurethane and/or polyurea block -[-G-]- containing oligomers of organic polymers; and/or
(iii) by the repetition of a polysiloxane block -[-L-]-.

A process for the synthesis of the block polycondensation products used in the scope of the invention will now be developed in greater detail. In its general features, this process corresponds to that already indicated at the beginning of the description.

In an organic solvent, a polysiloxane oligomer having a terminal diol function and/or a polysiloxane oligomer having a terminal diamine function, of general formula:

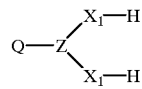

in which Q, Z and X, have the meanings defined above are reacted with a diisocyanate of formula:

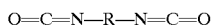

in which R has the signification given above.

If a final polycondensation product comprising polysiloxane blocks -[-L-]- is desired, the reaction is carried out, simultaneously with the diisocyanate in a sufficient quantity, of an α,ω-dihydroxy- and/or -diamino- and/or -aminohydroxy-polysiloxane of formula:

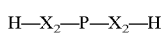

in which X$_2$ and P have the meanings indicated above, with stirring at a temperature ranging from 40 to 100° C., in the presence optionally of a catalyst of the tin salt type.

During this reaction the diisocyanate can be used in pure form or, preferably, in 50% solution in the same organic solvent used for the synthesis.

If the diisocyanate is aromatic (high reactive) no catalyst is used. If it is aliphatic or cycloaliphatic, a tin salt, such as dibutyltin dilaurate or tin 2-ethylhexanoate is preferably used as catalyst.

If it is desired to obtain a final polycondensation product comprising polyurethane and/or polyurea blocks -[-N-]- and/or -[-G-]-, in a second step the chains of the polycondensation product obtained previously are coupled by a diol and/or a diamine and/or an alcohol-amine, or mixtures of these reagents, of formula:

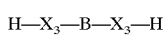

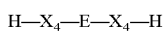

in which B, E, X$_3$ and X$_4$ have the meanings indicated above.

The coupling agents are introduced into the reaction medium in a preferably concentrated solution (preferably greater than or equal to 50% by weight) in a solvent which is either identical to that of the first step or compatible with the initial solution. Reaction is then allowed to take place for at least two hours at a temperature of 40 to 100° C.

When the first step has been carried out, the quantity of diisocyanate required for chain extension is introduced, or else this quantity is already present at the outset.

To obtain blocks -[-N-]- use will preferably be made of coupling agents H—$X_3$—B—$X_3$—H in the form of mixtures of nonionic coupling agents and ionizable coupling agents.

If an anionic polymer is the desired final product, it is advantageous to use dimethylol-propionic acid as anionizable coupling agent of formula:

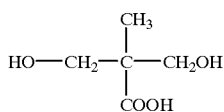

If a cationic polymer is a desired final product, it is advantageous to use N-methyldiethanolamine of formula:

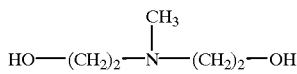

Once the coupling agent or mixture of coupling agents has been introduced, reaction is allowed to take place for about an hour, with stirring and at a temperature which is preferably equal to the boiling point of the solvent used.

A catalyst is then added in order to obtain a complete chain-coupling reaction. This catalyst is preferably a tin salt as defined above.

The mixture is again left to react for about eight hours with stirring and at a temperature ranging from 40 to 100° C.

The organic solvent used in these steps is preferably chosen from the group comprising acetone, methyl ethyl ketone, tetrahydrofuran and 1,2-dichloroethane, these solvents being inert with respect to isocyanate groups.

Within the context of the employment of the above process, particularly preferred diisocyanates are chosen, individually or in mixtures, from diphenylmethane 4,4'-diisocyanate and methylenebisdicyclohexyl 4,4'-diisocyanate, and particularly preferred coupling agents are chosen, individually or in mixtures, from dimethylolpropionic acid, N-methyldiethanolamine, 1,3-diaminopropane and ethanolamine, it being understood of course that the possibility of a mixture of acidic coupling agent/amine coupling agent is inadvisable.

So that the reaction of the second step is complete, it is necessary to remain in a homogeneous medium. To this end it is possible to add another solvent in addition which can be, for example, dimethylformamide or N-methylpyrrolidone, in a sufficiently low quantity to render the reaction medium homogeneous.

When the final polymer obtained is used in the form of a solution in an organic solvent, the polymer formed is purified by precipitation in a nonsolvent and drying of the precipitate thus obtained. The final purified polymer can then be dissolved in the solvent or solvents chosen for the cosmetic application.

When the final polycondensation product obtained is used in the form of an aqueous dispersion (pseudo-latex) it can be purified, for example, in a nonpolar solvent, such as cyclohexane, and then prepared according to the process which will be set out below.

The term "pseudo-latex" refers, according to the invention and in conformity with what is generally accepted, to a stable aqueous suspension comprising fine particles, generally spherical, of the polycondensation product as defined above, these particles having been obtained by the dispersion in an appropriate aqueous phase of the said polycondensation product in its ready-synthesized state.

The term "pseudo-latex" should not be confused with the expression "latex" or "synthetic latex" which is, indeed, likewise an aqueous suspension comprising particles of a polymer or polycondensation product but in which the particles have, conventionally, been obtained directly by emulsion polymerization (or, respectively, by polycondensation) of one or more monomers in an appropriate aqueous phase.

In particular, the synthesis of a "latex" necessarily involves the use of surfactants which are then always found in the final suspension.

The polycondensation products of the invention which are appropriate for dispersion in water are those whose chain is formed from polyurethane and/or polyurea blocks -[-N-]- and/or [-G-]- comprising ionizable groups to a sufficient extent.

In accordance with the invention these polycondensation products, which are optionally purified, can subsequently be used in the preparation of a stable pseudo-latex which will be made up of solid particles of the said polycondensation product neutralized with the aid of a suitable neutralizing agent, which may be either an organic or inorganic base when the radical B (and/or the radical E) as defined above carries anionizable functions such as, for example, sulphonic and/or carboxylic acid functions, or an organic or inorganic acid when the said radical B (and/or the radical E) carries cationizable functions such as, for example, tertiary amine functions, or else an alkyl halide, with a view to proceeding specifically to the quaternization of tertiary amines. According to the invention, the degree of neutralization preferably ranges from 10 to 100%, and more preferably from 20 to 100%.

A conventional process for the preparation of a pseudo-latex comprises dissolving a water-insoluble polymer in an organic solvent which is soluble or partially soluble in water, introducing a surfactant, a mixture of surfactants or a protective colloid polymer, or else a surfactant(s)/protective colloid polymer mixture, into the organic polymer solution thus obtained, with the aim of obtaining effective stabilization of the particles, and then dispersing (emulsion) with stirring the dispersion thus obtained in water, and subsequently removing the organic solvent by evaporation under vacuum, to give an aqueous suspension of polymer particles coated with surfactant(s) and/or with protective colloid polymer.

In contrast, the partially or totally neutralized ionic functions of certain polyurethane/polyurea block polycondensation products used within the scope of the invention, impart to the polycondensation products a kind of "autodispersibility" in water, making it possible to obtain particularly stable pseudo-latices in the absence of any hydrophilic stabilizer, any surfactant or any protective colloid.

One skilled in the art knows that the nature of the neutralizing agent which will suitably be used to neutralize the polyurethane/polyurea polycondensation product will depend on the nature of the ionizable functions carried by this product.

When the polycondensation product comprises an anionizable function such as, for example, a sulphonic or carboxylic acid function, the neutralizing agent can be an inorganic base such as sodium hydroxide, potassium hydroxide or ammonia, or an organic base such as an amino alcohol, chosen in particular from 2-amino-2-methyl-1-propanol (AMP), triethanolamine, triisopropanolamine (TIPA), monoethanolamine, diethanolamine, tris(2-hydroxy-1-propyl)amine, 2-amino-2-methyl-1,3-propanediol (AMPD) and 2-amino-2-hydroxymethyl-1,3-propanediol, or else a diamine such as lysine.

When the polycondensation product comprises a cationizable function of the tertiary amine type, the neutralizing agent can be an inorganic acid such as hydrochloric acid or an organic acid such as lactic acid, glycolic acid or mandelic acid. The neutralizing agent can also be a quaternizing agent of the tertiary amine function, for example alkyl halides, and in particular methyl iodide or ethyl bromide.

Neutralization can be carried out either in situ in the solution of the polyurethane/polyurea polycondensation product in the organic solvent, by addition of the specified quantity of neutralizing agent, or during the preparation of the emulsion, the neutralizing agent in this case being in the aqueous phase of the emulsion.

The organic solvent used must be a volatile solvent or a mixture of such solvents which has a boiling point less than that of water and must, moreover, be miscible or partially miscible with water. Such an organic solvent is preferably chosen from acetone, methyl ethyl ketone, tetrahydrofuran, methyl acetate, ethyl acetate, isopropanol and ethanol.

After the partially neutralized, silicone-grafted, polyurea/polyurethane polycondensation product in the organic solvent has been obtained, an emulsion is then prepared by pouring an appropriate quantity of water, optionally containing an antifoam whose function will be to facilitate the subsequent evaporation of the organic phase, with stirring into the organic solution obtained.

As indicated previously it is possible, according to one variant of the process, to carry out the neutralization of the ionizable functions of the polycondensation product during the actual formation of the emulsion, by pouring in an aqueous solution containing the required quantity of neutralizing agent.

During the formation of the emulsion, stirring is preferably accomplished with the aid of a shearing disperser of the Moritz, Ultra-Turrax or Raineri type fitted with deflocculating blades.

The emulsion thus obtained is particularly stable, without the need to use a surfactant, to the extent that the ionic groups of the polyurethane/polyurea polycondensation product become located at the interface with the water and protect the droplets from coalescence by means of electrostatic repulsion.

After formation of the emulsion at a temperature ranging from ambient temperature to about 70° C., evaporation of the organic solvent is then carried out under reduced pressure until it has been removed completely, the evaporation preferably being accomplished with slight heating.

The final product thus obtained is a pseudo-latex, i.e. an aqueous particle dispersion of the film-forming, silicone-grafted, polyurethane/polyurea polycondensation product, which is devoid of any surfactant or any other hydrophilic stabilizer but is highly stable.

The mean size of the particles making up the pseudo-latex, and their polydispersity, can be regulated by varying the respective proportions of polycondensation product, organic solvent and water during the preparation of the said pseudo-latex, or by varying the degree of neutralization or the type of neutralizing agent.

The pseudo-latices thus obtained by the preparation process described above, as well as the process, are further subjects of the invention.

According to a particular embodiment of the pseudo-latices used within the scope of the present invention, the mean size of the particles making up the said pseudo-latex preferably ranges from 5 to 400 nanometers, and more preferably ranges from 10 to 250 nanometers.

The size polydispersity of the said particles, measured by quasi-elastic light scattering, is generally less than 0.5, more preferably less than 0.3.

The principal subject of the invention involves the use of the block polycondensation products containing silicone grafts, or their pseudo-latex forms as described above, in and for the production of cosmetic or dermatological compositions.

The cosmetic or dermatological compositions according to the invention may therefore be provided in the form of an aqueous dispersion and may contain the polymers of the invention in pseudo-latex form.

This type of composition is particularly suitable for the multiblock polycondensation products according to the invention whose chain comprises polyurethane and/or polyurea blocks having ionizable groups.

The cosmetic or dermatological compositions of the invention may be provided in the form of a solution of the silicone-grafted polycondensation product in an organic solvent; in the form of an "emulsion" or dispersion in water of a solution of the silicone-grafted polycondensation product in an organic solvent, or else in the form of an aqueous-organic solution of the silicone-grafted polycondensation product.

It is preferred to use organic solvents for the silicone-grafted polycondensation products of the invention which are cosmetically or dermatologically acceptable, such as those solvents of the ether type.

Depending on the type of application chosen, it is possible to use a water-miscible solvent or else a mixture of water-miscible solvents of which one (having the function of a diluent) evaporates before the water, so as to enable the polymer to be dissolved in a solvent in the presence of water throughout the period of drying of the formulation applied to the keratinous material treated.

Water-miscible solvents which may be mentioned include dimethoxyethane and a dimethoxyethanel diethoxyethane mixture.

It is also possible to choose a solvent or mixture of solvents for the polymers according to the invention which is or are water-immiscible, such as diethoxyethane. If the formulation envisaged requires the presence of water for the given application, the organic solution of the polymer can be dispersed or emulsified in water with stabilizers such as surfactants and/or gelling agents which are present in the aqueous phase. In this case, one of the organic solvents used to dissolve the polymer preferably has a boiling point greater than that of water. In particular, diethoxyethane can be used.

The compositions according to the invention therefore contain, in a cosmetically acceptable vehicle or medium, the polymers as described above, for applications as varied as those encountered, for example, in the field of hair care, make-up or skin care, or of any other cosmetic field in which the use of a film-forming substance is desired or desirable, the said substances having properties which are especially notable, in particular in terms of their film-forming properties and their sheen or gloss properties, their ability to conserve these properties overtime under the action of external agents (permanence), and also their properties of softness, lubricity and abrasion resistance.

Among the applications which the present invention is preferably aimed at, and the various beneficial effects obtained in the applications, more particular mention may be made of:

the field of hair care products (for washing, treating or beautifying hair) where the compositions according to the invention, in particular in the form of aerosols, foams, shampoos, conditioners, styling or treating gels or lotions, hair shaping or hair setting or else fixing lotions or lacquers, make it possible to impart to the hair sheen, softness, ease of styling (phenomenon of "individual separation" of the hair at the time of application of the composition), better feel, and permanence (i.e. long-term retention even under the action of external agents) of these properties.

The field of make-up products, in particular for making up the nails and eyelashes, where the compositions according to the invention, in the form of nail varnishes, mascaras or eyeliners, for example, make it possible to provide, in the case of eyelash make-up, the same advantages as those set out above for the treatment of hair, and, in the case of nail varnishes (where the compositions can be used as sole film-former or as film-forming additive), gloss, better wettability of the nail, permanence of the film and of its gloss under washing, better abrasion resistance (provision of slip properties by lubrication of the surfaces), and better rigidity.

In the field of skin care products (creams, milks, lotions, masks, sera, sun care products), where the compositions according to the invention make it possible in particular to provide sheen, better wettability and resistance to washing with water (sun care products).

The proportion of film-forming polymer in the cosmetic compositions generally ranges from 0.5 to 50%, and more preferably ranges from 1 to 20%, of the total weight of the composition. In the case of nail varnishes, this proportion is generally greater than or equal to 25% by weight.

Of course, the compositions may additionally comprise various adjuvants intended to render them acceptable in a particular cosmetic application.

The compositions according to the invention can contain UV-A or UV-B or broad-band sunscreens and can thus be used as anti-sun products.

The compositions according to the invention can moreover comprise conventional cosmetic additives chosen from fats, organic solvents, thickeners, emollients, antifoams, moisturizers, humectants, treatment agents (anti-hair-loss agents, anti-dandruff agents, etc.), antiperspirants, alkalifying agents, dyes, pigments, perfumes, preservatives and propellants when the compositions are in aerosol form.

They may additionally comprise silicones which are traditionally used in cosmetics and/or anionic, nonionic or amphoteric organic polymers which are compatible with polyurethanes or polyureas. The presence of the silicone grafts in the structure of the polycondensation products of the invention can make it possible to obtain good compatibility of these polymers with the silicones and the organic polymer additives, whose mutual compatibility is in general problematic in the absence of the polymers of the invention.

More precisely, as a fatty substance it is possible to use an oil or a wax or mixtures thereof, fatty acids, fatty alcohols, fatty acid esters, such as $C_6$–$C_{18}$ fatty acid triglycerides, petroleum jelly, paraffin, lanolin, or hydrogenated or acetylated lanolin.

Oils which may be mentioned include mineral oils, animal oils, vegetable oils or synthetic oils, and especially liquid paraffin, paraffin oil, castor oil, jojoba oil, sesame oil, silicone gums and oils, and isoparaffins.

Animal, fossil, plant, mineral or synthetic waxes which may be mentioned in particular are beeswax, carnauba wax, candellila wax, ozokerite, microcrystalline waxes and silicone waxes and resins.

Thickeners which may be mentioned include:

modified celluloses such as hydroxyethylcellulose, methylcellulose, hydroxypropylcellulose and carboxymethylcellulose. Among the latter particular mention may be made of the gums sold under the name "Cellosize QP 44001H" by Amercol, carob gum, guar gum, the quaternized guar gum sold under the name "Jaguar C-13-S" by Meyhall, hydroxypropylguar gum and xanthan gum, crosslinked polyacrylic acids such as the "Carbopol" grades from Goodrich, the polyglyceryl (meth)acrylate polymers sold under the names "Hispagel" or "Lubragel" by Hispano Quimica or Guardian, polyvinylpyrrolidone, polyvinyl alcohol, the crosslinked acrylamide and ammonium acrylate polymers sold under the names "PAS 5161" or "Bozepol C" by Hoechst, the crosslinked acrylamide and 2-acrylamido-2-methylpropanesulphonic acid polymers, partially or totally neutralized, which are sold under the name "Sepigel 305" by Seppic, the crosslinked acrylamide and methacryloyloxyethyltrimethylammonium chloride polymers sold under the name "Salcare SC95" by Allied Colloid, or else the crosslinked homopolymers of methacryloyloxyethyltrimethylammonium chloride sold under the name "Salcare SC95" by Allied Colloid.

The examples which follow serve to illustrate the invention without, however, presenting any limitation thereof.

EXAMPLES

The syntheses leading to the silicone-grafted polyurethane and/or polyurea block polycondensation products were carried out starting from the polysiloxane oligomer, containing a terminal diol function, of general formula:

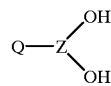

as defined above which is sold by Shinetsu under the name X22176 DX, having an average molecular weight of approximately 4000, measured at the top of the GPC peak, and an OH number of 26.7.

Example 1

In this example, a polycondensation product of theoretical structure:

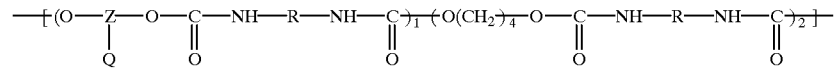

was prepared in which:

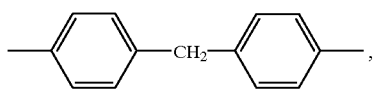

corresponding to the reaction between:
- 1 mole of X 22176 DX (polysiloxane oligomer),
- 2 moles of 1,4-butanediol (coupling agent),
- 1 mole of 4,4'-diphenylmethane diisocyanate (referred to as MDI hereinafter).

A solution of 100 g of oligomer X 22176 DX in 120 g of tetrahydrofuran (called THF subsequently) was introduced under a stream of nitrogen into a cylindrical reactor provided with a central stirrer of the anchor type, a thermometer, a condenser, a vacuum unit and a nitrogen bubbling unit and fitted at the top with a dropping funnel. A number of vacuum/nitrogen degassing operations were carried out in order to purge the air inside the reactor. Stirring was carried out at approximately 250 rpm. 17.9 g of solid MDI were then introduced rapidly into the medium under a stream of nitrogen, with stirring and at room temperature.

The solid was dissolved completely with stirring and the mixture was heated at 65 ° C (boiling of the solvent) for 3 hours.

A solution of 4.82 g of 1,4-butanediol in 50 g of THF was then added rapidly (via the dropping funnel). The mixture was then left to react with stirring at 65° C. for one hour.

0.05 g of (liquid) pure dibutyltin dilaurate catalyst was then added and the mixture was left to react at 65° C. for eight hours. At this point the coupling reaction was terminated.

The medium was brought back to room temperature. The synthesis solution was purified by precipitation in an ethanol/water (70:30 by weight) mixture. The precipitate was recovered and dried.

105 g of block polycondensation product are obtained.

Example 2

In this example, an emulsion was produced containing the polymer prepared in Example 1.

15 g of the said polymer were dissolved in diethoxyethane (boiling point 125° C.) so as to form a 4% by weight solution of polymer. This solution was emulsified in water after stabilization by an appropriate surfactant, to form a final emulsion containing 2% by weight of polymer.

This emulsion can be used for application to the hair after shampooing, thus forming a hair shaping lotion.

Example 3

In this example, an anionic polyurethane block polycondensation product with silicone grafts was prepared, of theoretical structure corresponding to the reaction between:
- 1 mole of X 22176 DX,
- 1 mole of 1,4-butanediol (coupling agent),
- 1 mole of dimethylolpropionic acid (called DMPA hereinafter; coupling agent),
- 3 moles of MDI.

The procedure continued under the same conditions as those of Example 1, using:
- 100 g of X 22176 DX,
- 120 g of THF,
- 17.9g of MDI.

The reaction took place at 65° C. for 3 hours.

A solution of a mixture of coupling agents was then introduced into the medium at 65° C. with stirring, the solution comprising:
- 2.4 g of 1,4-butanediol,
- 3.6 g of DMPA,
- 200 g of THF.

The reaction mixture was left to react for 1 hour at 65° C.

For the following examples, two identical polymer syntheses were carried out.

Example 4

In this example, an emulsion was produced from a polymer prepared in Example 3.

One of the two syntheses of Example 3 was purified by precipitating the synthesis solution in water.

115 g of polymer were thus obtained with an acid number $I_A$ of 10 after drying.

100 g of the polymer obtained were dissolved in a 50:50 by weight mixture of dimethoxyethane (boiling point 85° C.) and diethoxyethane (boiling point 125° C.) in order to form a 25% solution of polymer.

The polymer, dissolved with 2-amino-2-methylpropanol (called AMP hereinafter), was neutralized to a degree of neutralization of 70% in accordance with the acid number of the polymer (i.e. 1.11 g of AMP).

This solution was auto-emulsified in water as follows.

The organic solution was stirred vigorously using a shearing disperser of the Ultra-Turrax type, the 1.11 g of AMP dissolved in 50 ml of water were added in successive portions, and the mixture was then diluted by adding 500 g of deionized water, with continuous and vigorous stirring using the Ultra-Turrax.

An emulsion with a solids content of 12% was thus obtained. This could be concentrated to a solids content of 25% on a rotary evaporator.

By incorporating nonionic water-soluble active nail care agents into the said emulsion, a formulation was obtained which constituted a nail care base providing a protective film.

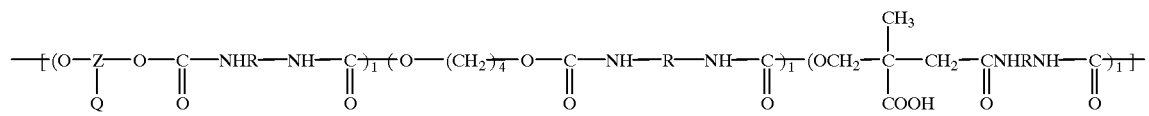

Similarly, this emulsion, diluted with water to a final solids content of 5% of polymer, constituted a hair shaping formula which was applied to wet hair which was then dried with a hair dryer (after application of the emulsion).

Example 5

In this example a pseudo-latex was produced from the polymer obtained in the second synthesis of Example 3.

450 g of the synthesis solution were introduced into a beaker (at a concentration of 24% of polymer, the acid number of the polymer $I_A$ is 10).

This solution was stirred vigorously using a dispersing stirrer of the Ultra-Turrax type.

A solution comprising 0.85 g of AMP in 50 ml of deionized water was introduced little by little (for 50% neutralization of the polymer).

With continuous and vigorous stirring using the Ultra-Turrax, the emulsion was diluted by gradually adding 900 g of deionized water.

The emulsion thus obtained was concentrated on a rotary evaporator in order to remove the organic solvent (THF) and part of the water.

A stable pseudo-latex (350 g) was thus obtained with a solids content of 37%, which had the following characteristics:

mean particle size 180 nm, size polydispersity <0.1.

These particle sizes were measured by quasi-elastic light scattering on a Coulter N4 SD from Coutronix.

Example 6

In this example a polycondensation product was prepared of theoretical structure:

$$\left[ (O-Z-O-\underset{Q}{\overset{|}{C}}-NHR-NH-\overset{O}{\overset{\|}{C}})_T(O-(CH_2)_4-O-\overset{O}{\overset{\|}{C}}-NH-R-NH-\overset{O}{\overset{\|}{C}})_T(O-(CH_2)_2-\underset{|}{\overset{CH_3}{N}}-(CH_2)_2-O-\overset{O}{\overset{\|}{C}}NHRNH-\overset{O}{\overset{\|}{C}})_T \right]$$

in which R denotes: —⟨phenyl⟩—CH₂—⟨phenyl⟩—, corresponding to the reaction between:

1 mole of X 22176 DX, 1 mole of 1,4-butanediol (coupling agent), 1 mole of N-methyldiethanolamine (called MEA below; coupling agent), 3 moles of MDI.

The procedure was carried out under the same conditions as those of Example 1, using:

100 g of oligomer X 22176 DX, 120 g of THF, 17.9 g of MDI.

The reaction took place at 65° C. for 3 hours.

A solution of a mixture of coupling agents was then introduced into the medium at 65° C. with stirring, this solution comprising:

2.145 g of 1,4-butanediol, 2.84 g of N-methyldiethanolamine (MEA), 200 g of THF.

The mixture was left to react at 65° C. for one hour.

The following procedure was identical to the process of Example 1 (for the coupling).

Two syntheses of this polymer were carried out.

Example 7

In this example a pseudo-latex was produced from the first synthesis of Example 6.

455 g of the solution from the previous synthesis containing 27% of polymer (i.e. 123 g of the polymer) were introduced into a beaker. This solution was stirred vigorously using the Ultra-Turrax.

A solution comprising:

11.6 g of 2M HCI 50 ml of deionized water (in order to neutralize the polymer 100% in accordance with its amine number) was introduced in portions into the medium, with stirring.

500 g of deionized water were then added, still with vigorous agitation.

The emulsion obtained was then concentrated on a rotary evaporator in order to remove completely the organic synthesis solvent (THF) and to concentrate the product in water.

A pseudo-latex was thus obtained with a final solids content of 27%, which had the following characteristics:

mean particle size: 100 nm, size polydispersity: 0.14.

Example 8

In this example an emulsion was produced from the second synthesis of Example 6.

The polymer was purified by precipitation in water and dried.

100 g of the polymer were dissolved to a concentration of 25% in a mixture of dimethoxyethane/diethoxyethane (50:50 by weight).

The solution obtained was stirred using the Ultra-Turrax.

A solution comprising:

11.6 g of 2 M HCI and 50 ml of deionized water was added in portions, and progressive dilution was then carried out with 500 g of deionized water, so as to obtain a stable emulsion with a solids content of 12%.

When the emulsion obtained was diluted to a concentration of 5% with water, a formulation for a hair shaping lotion was obtained.

Example 9

The following is a formulation example for nail varnish.

| | |
|---|---|
| Pseudo-latex of Example 5 | 25 g of active substance |
| Nonionic urethane associative thickener sold under the name "SER AD FX 1100" by Servo | 0.3 g |

-continued

| | |
|---|---|
| Pigments | 1 g |
| Water qs | 100 g |

The nail varnish obtained was highly water-resistant: the film was intact after 1 hour in water with stirring.

The film obtained adhered properly to the nail keratin without flaking. It was not tacky and was scratch-resistant.

The varnish obtained according to the invention could be applied easily to the nail and additionally presented a very good gloss and a satisfactory hold.

Example 10

This example illustrates a formulation for mascaras.

| | |
|---|---|
| Phase A: | |
| triethanolamine stearate | 11.8 g |
| beeswax | 5 g |
| carnauba wax | 3 g |
| paraffin | 1 g |
| Phase B: | |
| black iron oxide | 5 g |
| Phase C: | |
| gum arabic | 2 g |
| hydroxyethylcellulose sold under the name "Cellosize QP" by Amerchol | 1.2 g |
| Phase D: | |
| pseudo-latex of Example 5 | 5 g of active substance |
| preservative qs | |
| water qs | 100 g |

This mascara was obtained by bringing the ingredients of phase A to 85° C., adding phase B and stirring the mixture using a turbine stirrer.

The water for the preparation was then brought to boiling point, the preservatives were added, followed at 85° C. by the ingredients of phase C.

The aqueous phase obtained (85° C.) was then added to phase A (85° C.) with stirring using a turbine stirrer (emulsification) before finally adding, at 30° C., the pseudo-latex of phase D and stirring the mixture using a paddle stirrer.

Example 11

This example illustrates an alternative composition for mascaras. This mascara was prepared according to the same method as that given in Example 10 but using the following constituents:

| | |
|---|---|
| Phase A: | |
| glycerol stearate | 3 g |
| mixture of esters of lauric acid and sorbitol and of lauric acid and sorbitol ethoxylated with 20 moles of ethylene oxide, sold under the name "Tween 20" by ICI | 3.7 g |
| monoesters of stearic acid and sorbitan sold under the name "Span 60" by ICI | 5.6 g |
| beeswax | 6 g |

-continued

| | |
|---|---|
| carnauba wax | 1.8 g |
| paraffin | 7.8 g |
| Phase B: | |
| black iron oxide | 4.5 g |
| Phase C: | |
| hydroxyethylcellulose sold under the name "Cellosize QP" by Amerchol | 1.5 g |
| Phase D: | |
| pseudo-latex of Example 7 | 20 g |
| preservatives qs | |
| water qs | 100 g |

Example 12

Various examples of hair care formulations are given.

| Shampoo: | |
|---|---|
| pseudo-latex of Example 5 | 5 g of active substance |
| sodium lauryl ether sulphate | 15 g |
| cocoylbetaine in 32% aqueous solution, sold under the name of "Chimexane HC" by Chimex | 3 g of active substance |
| fragrances, preservatives, qs | |
| demineralized water qs | 100 g |

| Shampoo: | |
|---|---|
| pseudo-latex of Example 7 | 5 g of active substance |
| sodium lauryl ether sulphate | 15 g |
| cocoylbetaine in 32% aqueous solution | 3 g of active substance |
| fragrances, preservatives, qs | |
| demineralized water qs | 100 g |

| Hair shaping lotion: | |
|---|---|
| pseudo-latex of Example 5 | 5 g of active substance |
| fragrances, dyes, preservatives qs | |
| demineralized water qs | 100 g |

This composition, applied to the hair after a shampoo, gave the hairstyle good form retention and imparted an excellent sheen to the hair.

| Hair shaping lotion: | |
|---|---|
| pseudo-latex of Example 7 | 5 g of active substance |
| fragrances, dyes, preservatives qs | |
| demineralized water qs | 100 g |

This composition, applied to the hair after a shampoo, gave the hairstyle good form retention and imparted an excellent sheen to the hair.

Hair spray:

A hair spray in a pump flask was prepared by packaging, in an appropriate container, the following composition:

| | |
|---|---|
| pseudo-latex of Example 5 | 3 g of active substance |
| fragrances, dyes, preservatives, qs | |
| demineralized water qs | 100 g |

Once filled, the container was then provided with a spray pump.

This composition gave the hairstyle a good hold and imparted excellent sheen to the hair.

Hair spray:

A hair spray was prepared by mixing:

| | |
|---|---|
| pseudo-latex of Example 7 | 3 g of active substance |
| fragrances, dyes, preservatives, qs | |
| demineralized water qs | 100 g |

The lotion obtained was then packaged in a rechargeable compressed-air spray device.

This composition gave the hairstyle a good hold and imparted excellent sheen to the hair.

We claim:

1. A method for cosmetically treating keratinous material, comprising the steps of applying to said keratinous material a cosmetically effective amount of a composition comprising at least one polyurethane and/or polyurea block polycondensation product, wherein said product comprises a chain containing the repetition of at least one polyurethane and/or polyurea block -{-M-}- having the following formula (I):

$$-\{\{X_1-D-X_1\}-\underset{O}{\overset{\|}{C}}-NH-R-NH-\underset{O}{\overset{\|}{C}}\}-$$ (I)

wherein $X_1$ independently represents —O— or —NH—;

D represents a segment of formula:

in which Z is a trivalent hydrocarbon radical which may comprise one or more heteroatoms; and Q is a polysiloxane segment; and R is a divalent radical chosen from aliphatic, cycloaliphatic, and aromatic radicals, wherein said block -{-M-}- includes a polysiloxane graft, and wherein said product is present in a cosmetically or dermatologically acceptable medium.

2. A method according to claim 1, wherein said segment Q is of the formula (I'):

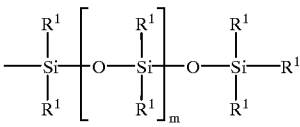

wherein the radicals $R^1$ are independently selected from $C_1$–$C_{20}$ monovalent hydrocarbon, halohydrocarbon, and perhalogenated radicals which are free or substantially free from ethylenic unsaturation, and aromatic radicals; and m is an integer such that the average molecular weight, measured at the top of the GPC peak, of the polysiloxane segment, ranges from 300 to 50,000.

3. A method according to claim 2, wherein the average molecular weight, measured at the top of the GPC peak, of the polysiloxane segment, ranges from 500 to 20,000.

4. A method according to claim 2, wherein said radicals $R^1$ are independently selected from alkyl radicals, cycloalkyl radicals, aryl radicals, and arylalkyl radicals.

5. A method according to claim 4, wherein said alkyl radicals are selected from methyl, ethyl, propyl, isopropyl, butyl, pentyl, hexyl, octyl, decyl, dodecyl and octadecyl radicals; said cycloalkyl radicals are cyclohexyl radicals; said aryl radicals are selected from phenyl, naphthyl, tolyl and xylyl radicals; and said arylalkyl radicals are selected from benzyl and phenylethyl.

6. A composition according to claim 1, wherein Z is a trivalent radical selected from radicals corresponding to the formulae:

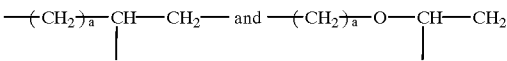

wherein a represents an integer ranging from 1 to 10.

7. A method according to claim 1, wherein said radical R is selected from radicals of the formulae:

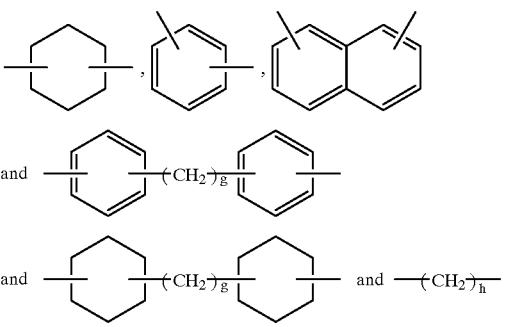

wherein g is an integer ranging from 0 to 3; and h is an integer ranging from 1 to 20.

8. A method according to claim 7, wherein h ranges from 2 to 12.

9. A method according to claim 1, wherein said composition is provided in the form of a solution of said at least one polyurethane and/or polyurea block polycondensation product containing silicone grafts in an organic solvent; in the form of an "emulsion" or in the form of a dispersion in water of a solution of said at least one polycondensation product in an organic solvent; or in the form of an aqueous-organic solution of said at least one polycondensation product.

10. A method according to claim 1, wherein the composition comprises, by weight relative to the total weight of the composition, from 0.5 to 50% of said at least one polyurethane and/or polyurea block polycondensation product.

11. A method according to claim 1, wherein said composition is a composition to be used on hair, a make-up composition, or a skin-care composition.

12. A method according to claim 1, wherein said composition additionally comprises at least one additive chosen from fats, organic solvents, thickeners, emollients, antifoams, moisturizers, humectants, treatment agents, antiperspirants, alkifying agents, dyes, pigments, fragrances, preservatives, propellants, silicones, anionic, nonionic and amphoteric organic polymers which are compatible with polyurethanes or polyureas, UV-A sunscreens, UV-B sunscreens and water.

* * * * *

UNITED STATES PATENT AND TRADEMARK OFFICE
CERTIFICATE OF CORRECTION

PATENT NO. : 6,166,093
DATED : December 26, 2000
INVENTOR(S) : Mougin et al.

It is certified that error appears in the above-identified patent and that said Letters Patent is hereby corrected as shown below:

<u>Column 24,</u>
Line 28, "composition" should read -- method --.

Signed and Sealed this

Sixteenth Day of July, 2002

*Attest:*

*Attesting Officer*

JAMES E. ROGAN
*Director of the United States Patent and Trademark Office*